(12) United States Patent
Kumar et al.

(10) Patent No.: US 6,218,136 B1
(45) Date of Patent: Apr. 17, 2001

(54) METHODS OF THE IDENTIFICATION OF PHARMACEUTICALLY ACTIVE COMPOUNDS

(75) Inventors: Sanjay Kumar, King of Prussia; George Pietro Livi, Havertown; Megan McHale McLaughlin, Drexel Hill, all of PA (US); Peter Ronald Young, Lawrenceville, NJ (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/142,551
(22) PCT Filed: Mar. 12, 1997
(86) PCT No.: PCT/US97/04256
§ 371 Date: Sep. 10, 1998
§ 102(e) Date: Sep. 10, 1998
(87) PCT Pub. No.: WO97/34137
PCT Pub. Date: Sep. 18, 1997

Related U.S. Application Data

(60) Provisional application No. 60/013,286, filed on Mar. 12, 1996.

(51) Int. Cl.$^7$ .............................. C12Q 1/48; C12Q 1/68; C12N 9/12
(52) U.S. Cl. .............................. 435/15; 435/6; 435/194; 514/12; 514/789
(58) Field of Search .................... 435/15.6, 194; 514/789, 12

(56) References Cited

PUBLICATIONS

McLaughlin, et al., "Identification of Mitogen–activated Protein (MAP) Kinase–activated Protein Kinase–3, a Novel Substrate of CSBP p38 MAP Kinase," *Journal of Biological Chemistry*, 271(14): pp. 8488–8492 (1996).

Cuenda, et al., "SB 203580 is a specific inhibitor of a MAP kinase homologue which is stimulated by cellular stresses and interleukin–1," *FEBS Letters* 364: pp. 229–233 (1995).

*Primary Examiner*—Rebecca E. Prouty
(74) *Attorney, Agent, or Firm*—Elizabeth J. Hecht; William T. King; Charles M. Kinzig

(57) ABSTRACT

CSBP/p38 is a MAP kinase that is activated in response to stress, endotoxin, interleukin 1 and tumor necrosis factor. Using a catalytically inactive mutant (D168A) of human CSBP2 as the bait in a yeast two-hybrid screen, a kinase has been cloned which shares ~70% amino acid identity to MAPKAP kinase-2, and thus was designated MAPKAP kinase-3. The binding of CSBP to MAPKAP kinase 3 was confirmed in vitro by the precipitation of epitope-tagged CSBP1, CSBP2 and CSBP2(D168A) and endogenous CSBP from mammalian cells by a bacterially-expressed GST-MAPKAP kinase-3 fusion protein and in vivo by co-precipitation of the epitope-tagged proteins co-expressed in HeLa cells. MAPKAP kinase-3 was phosphorylated by both CSBP1 and CSBP2, and was then able to phosphorylate HSP27 in vitro. Treatment of HeLa cells with sorbitol or TNF resulted in activation of CSBP and MAPKAP kinase-3 and activation of MAPKAP kinase-3 could be blocked by preincubation of cells with 4-(4-Fluorophenyl)-2-(4-methylsulfinylphenyl)-5-4-pyridyl)-1H-imidazole, a specific inhibitor of CSBP kinase activity. These data suggest that MAPKAP kinase-3 is activated by stress and cytokines and is a novel substrate of CSBP both in vitro and in vivo. The use of MAPKAP kinase-3 in screens for the identification of pharmaceutically active compounds is disclosed.

16 Claims, 4 Drawing Sheets

```
MAPKAPK3  MDGETAEEQGGPVP----PPVAPGGPLGGAPGGRREP---------------KKYAV      39
MAPKAPK2A ----S-QGQSPPVPFPAPAPPPQPFTPALPHPPAQPPPPPPPPPQQFPQFHVKSGLQIKKNAI  55
MAPKAPK2B MLSNS-QGQSPPVPFPAPAPPPQPFTPALPHPPAQPPPPPPPPPQQFPQFHVKSGLQIKKNAI  59
                            I                II              III

MAPKAPK3  TDDYQLSKQVLGLGVNGKVLECFHRRTGQKCALKLLYDSPKARQEVDHHWQASGGPHIVC      99
MAPKAPK2A IDDYKVTSQVLGLGINGKVLQIFNKRTQEKFALKMLQDCPKARREVELHWRASQCPDIVR     115
MAPKAPK2B IDDYKVTSQVLGLGINGKVLQIFNKRTQEKFALKMLQDCPKARREVELHWRASQCPHIVR     119
                  IV                        V                 VIA

MAPKAPK3  ILDVYENMHHGKRCLLIIMECMEGGELFSRIQERGDQAFTEREAAEIMRDIGTAIQFLHS    159
MAPKAPK2A IVDVYENLYAGRKCLLIVMECLDGGELFSRIQDRGDQAFTEREASEIMKSIGEAIQYLHS    175
MAPKAPK2B IVDVYENLYAGRKCLLIVMECLDGGELFSRIQDRGDQAFTEREASEIMKSIGEAIQYLHS    179
                                                                  VIII

MAPKAPK3  HNIAHRDVKPENLLYTSKEKDAVLKLTDFGFAKETT-QNALQTPCYTPYYVAPEVLGPEK    218
MAPKAPK2A INIAHRDVKPENLLYTSKRPNAILKLTDFGFAKETTSHNSLTTPCYTPYYVAPEVLGPEK    235
MAPKAPK2B INIAHRDVKPENLLYTSKRPNAILKLTDFGFAKETTSHNSLTTPCYTPYYVAPEVLGPEK    239
                    VIB                      VII               X

MAPKAPK3  YDKSCDMWSLGVIMYILLCGFPPFYSNTGQAISPGMKRRIRLGQYGFPNPEWSEVSEDAK    278
MAPKAPK2A YDKSCDMLVLGVIMYILLCGYPPFYSNHGLAISPGMKTRIRMGQYEFPNPEWSEVSEEVK    295
MAPKAPK2B YDKSCDMWSLGVIMYILLCGYPPFYSNHGLAISPGMKTRIRMGQYEFPNPEWSEVSEEVK    299
                        IX

MAPKAPK3  QLIRLLLKTDPTERLTITQFMNHPWINQSMVVPQTPLHTARVLQEDKDHWDEVKEEMTSA    338
MAPKAPK2A MLIRNLLKTEPTQRMTITEFMNHPWIMQSTKVPQTPLHTSRVLKEDKERWEDVKEEMTSA    355
MAPKAPK2B MLIRNLLKTEPTQRMTITEFMNHPWIMQSTKVPQTPLHTSRVLKEDKERWEDVKGCLHD-    359
                XI

MAPKAPK3  LATMRVDYDQVKIK DLKTSNNRLLN KRRKK QAGSSSASQGCNNQ                  382
MAPKAPK2A LATMRVDYEQIKIK IEDASNPLLL KRRKK ARALEAAALA----H                  396
MAPKAPK2B ------------- ---KNSDQATW LTR---------------L                  370
```

Fig. 1

Fig. 2
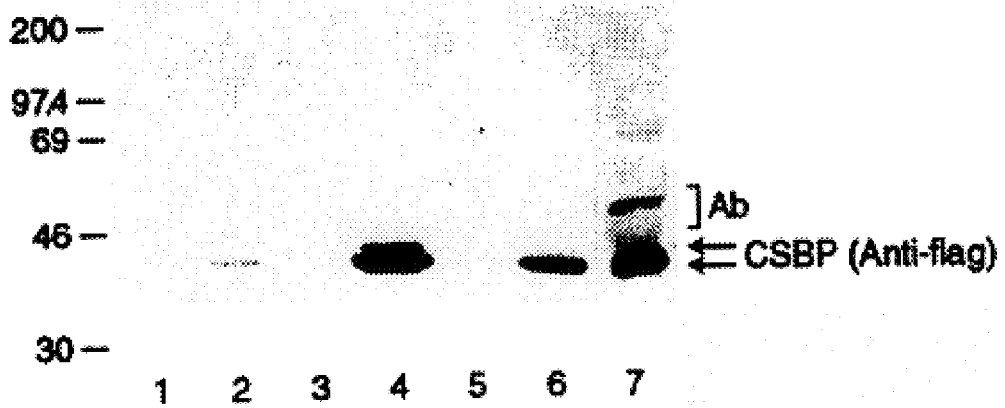
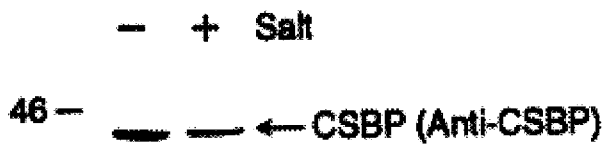
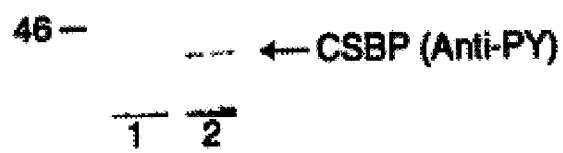

SEQUENCE LISTING

<160> NUMBER OF SEQ ID NOS: 4

<210> SEQ ID NO 1
<211> LENGTH: 1333
<212> TYPE: DNA
<213> ORGANISM: Homo sapiens

<400> SEQUENCE: 1

```
cgcggccgcg tcgacctctg agcgccccgc gggggccatg gatggtgaaa cagcagagga      60
gcagggggc cctgtgcccc cgccagttgc acccggcgga cccggcttgg gcggtgctcc      120
ggggggcgg cgggagccca agaagtacgc agtgaccgac gactaccagt tgtccaagca      180
ggtgctgggc ctgggtgtga acggcaaagt gctggagtgc ttccatcggc gcactggaca      240
gaagtgtgcc ctgaagctcc tgtatgacag ccccaaggcc cggcaggagg tagaccatca      300
ctggcaggct tctggcggcc cccatattgt ctgcatcctg gatgtgtatg agaacatgca      360
ccatggcaag cgctgtctcc tcatcatcat ggaatgcatg gaaggtggtg agttgttcag      420
caggattcag gagcgtggcg accaggcttt cactgagaga gaagctgcag agataatgcg      480
ggatattggc actgccatcc agtttctgca cagccataac attgcccacc gagatgtcaa      540
gcctgaaaac ctactctaca catctaagga gaaagacgca gtgcttaagc tcaccgattt      600
tggctttgct aaggagacca cccaaaaatgc cctgcagaca ccctgctata ctccctatta      660
tgtggcccct gaggtcctgg gtccagagaa gtatgacaag tcatgtgaca tgtggtccct      720
gggtgtcatc atgtacatcc tcctttgtgg cttcccaccc ttctactcca acacgggcca      780
ggccatctcc ccggggatga agaggaggat tcgcctgggc cagtacggct tccccaatcc      840
tgagtggtca gaagtctctg aggatgccaa gcagctgatc cgcctcctgt tgaagacaga      900
ccccacagag aggctgacca tcactcagtt catgaaccac ccctggatca accaatcgat      960
ggtagtgcca cagaccccac tccacacggc ccgagtgctg caggaggaca agaccactg     1020
ggacgaagtc aaggaggaga tgaccagtgc ccactatgcg ggtagactac gaccaggtga     1080
agatcaagga cttggcctga agacctctaa caaccggctc ctcaacaaga ggagaaaaaa     1140
gcaggcaggc agctcctctg cctcacaggg ctgcaacaac cagtagctca tggggccttg     1200
gaggagcctg gcctctcagc ctgcataaca gactgaaatg tgctcaggcc ctggccagga     1260
gggcccaggg tcattctttt aacaaaagga ttattttgtt gtgtttcaaa aaagtcgacg     1320
cggccgcgaa ttc                                                       1333
```

<210> SEQ ID NO 2
<211> LENGTH: 382
<212> TYPE: PRT
<213> ORGANISM: Homo sapiens

<400> SEQUENCE: 2

```
Met Asp Gly Glu Thr Ala Glu Glu Gln Gly Gly Pro Val Pro Pro Pro
 1               5                  10                  15

Val Ala Pro Gly Gly Pro Gly Leu Gly Gly Ala Pro Gly Gly Arg Arg
            20                  25                  30

Glu Pro Lys Lys Tyr Ala Val Thr Asp Asp Tyr Gln Leu Ser Lys Gln
        35                  40                  45

Val Leu Gly Leu Gly Val Asn Gly Lys Val Leu Glu Cys Phe His Arg
    50                  55                  60

Arg Thr Gly Gln Lys Cys Ala Leu Lys Leu Leu Tyr Asp Ser Pro Lys
```

```
           65                  70                  75                  80
Ala Arg Gln Glu Val Asp His His Trp Gln Ala Ser Gly Gly Pro His
                    85                  90                  95

Ile Val Cys Ile Leu Asp Val Tyr Glu Asn Met His His Gly Lys Arg
            100                 105                 110

Cys Leu Leu Ile Ile Met Glu Cys Met Glu Gly Gly Glu Leu Phe Ser
            115                 120                 125

Arg Ile Gln Glu Arg Gly Asp Gln Ala Phe Thr Glu Arg Glu Ala Ala
        130                 135                 140

Glu Ile Met Arg Asp Ile Gly Thr Ala Ile Gln Phe Leu His Ser His
145                 150                 155                 160

Asn Ile Ala His Arg Asp Val Lys Pro Glu Asn Leu Leu Tyr Thr Ser
                165                 170                 175

Lys Glu Lys Asp Ala Val Leu Lys Leu Thr Asp Phe Gly Phe Ala Lys
            180                 185                 190

Glu Thr Thr Gln Asn Ala Leu Gln Thr Pro Cys Tyr Thr Pro Tyr Tyr
            195                 200                 205

Val Ala Pro Glu Val Leu Gly Pro Glu Lys Tyr Asp Lys Ser Cys Asp
        210                 215                 220

Met Trp Ser Leu Gly Val Ile Met Tyr Ile Leu Leu Cys Gly Phe Pro
225                 230                 235                 240

Pro Phe Tyr Ser Asn Thr Gly Gln Ala Ile Ser Pro Gly Met Lys Arg
                245                 250                 255

Arg Ile Arg Leu Gly Gln Tyr Gly Phe Pro Asn Pro Glu Trp Ser Glu
            260                 265                 270

Val Ser Glu Asp Ala Lys Gln Leu Ile Arg Leu Leu Leu Lys Thr Asp
        275                 280                 285

Pro Thr Glu Arg Leu Thr Ile Thr Gln Phe Met Asn His Pro Trp Ile
290                 295                 300

Asn Gln Ser Met Val Val Pro Gln Thr Pro Leu His Thr Ala Arg Val
305                 310                 315                 320

Leu Gln Glu Asp Lys Asp His Trp Asp Glu Val Lys Glu Glu Met Thr
                325                 330                 335

Ser Ala Leu Ala Thr Met Arg Val Asp Tyr Asp Gln Val Lys Ile Lys
            340                 345                 350

Asp Leu Lys Thr Ser Asn Asn Arg Leu Leu Asn Lys Arg Arg Lys Lys
            355                 360                 365

Gln Ala Gly Ser Ser Ser Ala Ser Gln Gly Cys Asn Asn Gln
        370                 375                 380

<210> SEQ ID NO 3
<211> LENGTH: 396
<212> TYPE: PRT
<213> ORGANISM: Homo sapiens

<400> SEQUENCE: 3

Ser Gln Gly Gln Ser Pro Pro Val Pro Phe Pro Ala Pro Ala Pro Pro
  1               5                  10                  15

Pro Gln Pro Pro Thr Pro Ala Leu Pro His Pro Pro Ala Gln Pro Pro
                20                  25                  30

Pro Pro Pro Pro Gln Gln Phe Pro Gln Phe His Val Lys Ser Gly Leu
            35                  40                  45

Gln Ile Lys Lys Asn Ala Ile Ile Asp Asp Tyr Lys Val Thr Ser Gln
        50                  55                  60
```

```
Val Leu Gly Leu Gly Ile Asn Gly Lys Val Leu Gln Ile Phe Asn Lys
 65                  70                  75                  80

Arg Thr Gln Glu Lys Phe Ala Leu Lys Met Leu Gln Asp Cys Pro Lys
                 85                  90                  95

Ala Arg Arg Glu Val Glu Leu His Trp Arg Ala Ser Gln Cys Pro Asp
                100                 105                 110

Ile Val Arg Ile Val Asp Val Tyr Glu Asn Leu Tyr Ala Gly Arg Lys
                115                 120                 125

Cys Leu Leu Ile Val Met Glu Cys Leu Asp Gly Gly Glu Leu Phe Ser
130                 135                 140

Arg Ile Gln Asp Arg Gly Asp Gln Ala Phe Thr Glu Arg Glu Ala Ser
145                 150                 155                 160

Glu Ile Met Lys Ser Ile Gly Glu Ala Ile Gln Tyr Leu His Ser Ile
                165                 170                 175

Asn Ile Ala His Arg Asp Val Lys Pro Glu Asn Leu Leu Tyr Thr Ser
                180                 185                 190

Lys Arg Pro Asn Ala Ile Leu Lys Leu Thr Asp Phe Gly Phe Ala Lys
                195                 200                 205

Glu Thr Thr Ser His Asn Ser Leu Thr Thr Pro Cys Tyr Thr Pro Tyr
210                 215                 220

Tyr Val Ala Pro Glu Val Leu Gly Pro Glu Lys Tyr Asp Lys Ser Cys
225                 230                 235                 240

Asp Met Leu Val Leu Gly Val Ile Met Tyr Ile Leu Leu Cys Gly Tyr
                245                 250                 255

Pro Pro Phe Tyr Ser Asn His Gly Leu Ala Ile Ser Pro Gly Met Lys
                260                 265                 270

Thr Arg Ile Arg Met Gly Gln Tyr Glu Phe Pro Asn Pro Glu Trp Ser
                275                 280                 285

Glu Val Ser Glu Glu Val Lys Met Leu Ile Arg Asn Leu Leu Lys Thr
                290                 295                 300

Glu Pro Thr Gln Arg Met Thr Ile Thr Glu Phe Met Asn His Pro Trp
305                 310                 315                 320

Ile Met Gln Ser Thr Lys Val Pro Gln Thr Pro Leu His Thr Ser Arg
                325                 330                 335

Val Leu Lys Glu Asp Lys Glu Arg Trp Glu Asp Val Lys Glu Glu Met
                340                 345                 350

Thr Ser Ala Leu Ala Thr Met Arg Val Asp Tyr Glu Gln Ile Lys Ile
355                 360                 365

Lys Lys Ile Glu Asp Ala Ser Asn Pro Leu Leu Ile Lys Arg Arg Lys
                370                 375                 380

Lys Ala Arg Ala Leu Glu Ala Ala Leu Ala His
385                 390                 395

<210> SEQ ID NO 4
<211> LENGTH: 370
<212> TYPE: PRT
<213> ORGANISM: Homo sapiens

<400> SEQUENCE: 4

Met Leu Ser Asn Ser Gln Gly Gln Ser Pro Val Pro Phe Pro Ala
 1               5                  10                  15

Pro Ala Pro Pro Gln Pro Thr Pro Ala Leu Pro His Pro Pro
                20                  25                  30

Ala Gln Pro Pro Pro Pro Pro Gln Gln Phe Pro Gln Phe His Val
                35                  40                  45
```

-continued

```
Lys Ser Gly Leu Gln Ile Lys Lys Asn Ala Ile Ile Asp Asp Tyr Lys
    50              55                  60
Val Thr Ser Gln Val Leu Gly Leu Gly Ile Asn Gly Lys Val Leu Gln
65              70                  75                  80
Ile Phe Asn Lys Arg Thr Gln Glu Lys Phe Ala Leu Lys Met Leu Gln
            85                  90                  95
Asp Cys Pro Lys Ala Arg Arg Glu Val Glu Leu His Trp Arg Ala Ser
            100                 105                 110
Gln Cys Pro Asp Ile Val Arg Ile Val Asp Val Tyr Glu Asn Leu Tyr
            115                 120                 125
Ala Gly Arg Lys Cys Leu Leu Ile Val Met Glu Cys Leu Asp Gly Gly
    130                 135                 140
Glu Leu Phe Ser Arg Ile Gln Asp Arg Gly Asp Gln Ala Phe Thr Glu
145             150                 155                 160
Arg Glu Ala Ser Glu Ile Met Lys Ser Ile Gly Glu Ala Ile Gln Tyr
                165                 170                 175
Leu His Ser Ile Asn Ile Ala His Arg Asp Val Lys Pro Glu Asn Leu
            180                 185                 190
Leu Tyr Thr Ser Lys Arg Pro Asn Ala Ile Leu Lys Leu Thr Asp Phe
        195                 200                 205
Gly Phe Ala Lys Glu Thr Thr Ser His Asn Ser Leu Thr Thr Pro Cys
    210                 215                 220
Tyr Thr Pro Tyr Tyr Val Ala Pro Glu Val Leu Gly Pro Glu Lys Tyr
225                 230                 235                 240
Asp Lys Ser Cys Asp Met Leu Val Leu Gly Val Ile Met Tyr Ile Leu
            245                 250                 255
Leu Cys Gly Tyr Pro Pro Phe Tyr Ser Asn His Gly Leu Ala Ile Ser
            260                 265                 270
Pro Gly Met Lys Thr Arg Ile Arg Met Gly Gln Tyr Glu Phe Pro Asn
        275                 280                 285
Pro Glu Trp Ser Glu Val Ser Glu Glu Val Lys Met Leu Ile Arg Asn
    290                 295                 300
Leu Leu Lys Thr Glu Pro Thr Gln Arg Met Thr Ile Thr Glu Phe Met
305             310                 315                 320
Asn His Pro Trp Ile Met Gln Ser Thr Lys Val Pro Gln Thr Pro Leu
            325                 330                 335
His Thr Ser Arg Val Leu Lys Glu Asp Lys Glu Arg Trp Glu Asp Val
        340                 345                 350
Lys Gly Cys Leu His Asp Lys Asn Ser Asp Gln Ala Thr Trp Leu Thr
        355                 360                 365
Arg Leu
370
```

METHODS OF THE IDENTIFICATION OF PHARMACEUTICALLY ACTIVE COMPOUNDS

This application claims benefit to U.S. provisional application Ser. No. 60/013286 filed Mar. 12, 1996.

FIELD OF THE INVENTION

This invention relates to methods for the identification of pharmaceutically active compounds. Specifically, this invention relates to methods for identification of compounds capable of affecting the interaction of an intermediate of a MAP (Mitogen Activated Protein) kinase cascade. More specifically, this invention relates to screening methods useful for detecting compounds having an effect on the activity and/or interaction of a MAPKAP (Mitogen Activated Protein Kinase-Activated Protein) kinase.

BACKGROUND OF THE INVENTION

Cytokines play an important role in regulating the cellular response during inflammation and other immune functions. Of particular interest are the cytokines interleukin-1 (IL-1, $\alpha$ and $\beta$) and tumor necrosis factor (TNF, $\alpha$ and $\beta$) which are the intercellular proteins involved in the initial step of the inflammatory response cascade (Arai, et al., Ann. Rev. Biochem, 59: 783–836 (1990). Thus, there has been a substantial amount of research recently devoted to interfering with the production of IL-1 and TNF in response to an inflammatory stimulus.

One therapeutic approach involves suppressing the production of IL-1 and TNF at the level of transcription and/or translation and/or secretion. The activities associated with certain of pyridinyl imidazoles led to a class of compounds referred to as CSAID™ compounds (FIG. 1). These compounds appear to arrest the expression of IL-1 and TNF predominantly at the translational level, although a lesser effect on transcription has also been observed but effects on other steps cannot be ruled out.

The pyridinyl imidazole, 5-(4-pyridyl)-6(4-fluorophenyl)-2,3-dihydroimidazo(2,1-b)thiazole (SK&F 86002) was identified as the prototypic CSAID™ compound. The basis for its activity has been established and characterized (Lee, et al., Int'l. J. Immunopharm, 10(7): 835–843 (1988); Agents and Actions 27(¾): 277–279 (1989) and Int'l. J. Immunother, 6(1):1–12 (1990)). SAR studies suggest that cytokine suppressive effect of the pyridinyl imidazoles represents a unique activity independent of their inhibitory effects on eicosanoid and leukotriene production. However, no compound of the initial series was selective for cytokine suppressive activity or was particularly potent.

Since the CSAID™ compounds have substantial potential, inter alia, as novel anti-inflammatory therapeutic agents, there is significant interest in characterizing their mechanism of action at the molecular level, as well as obtaining compounds with increased selectivity and potency. One approach involves the identification and characterization of the molecular targets thereby enhancing the understanding of the biochemical processes involved in inflammation and aid in the design and screening of more potent anti-inflammatory drugs. PCT application WO 95/07922, published 23 March 1995, inter alia, discloses the purification and characterization of one such molecule, a CSAID binding protein (CSBP).

It is now appreciated that the binding of an effector cytokine to its receptor protein is just the first step in a cascade of events. One response to a variety of cellular stimuli, including cytokines, involves a series of protein kinase steps known as the MAP (mitogen-activated protein) kinase cascade. Ammerer, G. (1994) Curr. Opin. Genet. Dev. 4, 90–95; Cobb, et al., (1995) J. Biol. Chem. 270, 14843–14846; and Herskowitz, I., (1995) Cell 80, 187–197. Several genetically distinct MAP kinase pathways have been defined in yeast and at least three exist in mammalian cells.(Ammerer, supra and Cobb et al., supra). The mammalian MAP kinases include the extracellular signal regulated kinases (ERKs) the c-Jun N-terminal kinases (JNKs) and the CSBP/p38/RK/Mpk2 kinases.(Cobb et al., supra). These kinases are activated by distinct upstream dual specificity kinases (MAP kinase kinases) which phosphorylate both threonine and tyrosine in a regulatory TXY (Thr-Xaa-Tyr, where X is any amino acid) loop present in all MAP kinases.(Hanks et al., (1988) Science 241, 42–52.). Once activated, these MAP kinases phosphorylate their substrates on serine and/or threonine residues with attendant effects on their activity. For example, phosphorylation of c-Jun and ATF2 by JNK (Gupta, et al., (1995) Science 267, 389–393; and Derijard, et al., (1994) Cell 76, 1025–1037) stimulates their transcriptional activity.

CSBP (also known as p38, RK and mpk2) (Lee, et al., (1994) Nature 372, 739–746; Han, et al., (1994) Science 265, 80–881; and Rouse et al., (1994) Cell 78, 1027–1037) is the mammalian homologue of the yeast Hog1 protein which is required for growth of yeast in high osmolarity media (Brewster, et al., (1993) Science 259, 1760–1762) and it can partially complement a hog1 deficiency in yeast.(Han et al., supra; and Kumar, et al. (1995) J. Biol. Chem. 270, 29043–29046). CSBP is activated in mammalian cells by environmental or chemical stress such as hyperosmolarity, UV light, heat shock, arsenite, and endotoxin or cytokines such as interleukin-1 (IL-1) and tumor necrosis factor (TNF) (Lee, et al., supra; Han, et al., supra; Rouse et al, supra; Freshney, et al., (1994) Cell 78, 1039–1049; and Raingeaud, et al., (1995) J. Biol. Chem. 270, 7420–7426). In response to stress, CSBP kinase activity is activated through phosphorylation by at least two MAP kinase kinases, MKK3 and MKK4 (also known as SAPK) (Derijard, et al., (1995) Science 267, 682–685; and Lin et al., (1995). Science 268, 286–290). Of the in vitro substrates of CSBP which include MAPKAP kinase-2.(Rouse et al., supra; Freshney et al., supra; and Cuenda, et al., (1995) FEBS Lett. 364, 229–231), myelin basic protein (MBP) (Lee et al., supra; and Kumar et al., supra), and ATF2 (Derijard, et al., supra), only MAPKAP kinase-2 is known to be an in vivo substrate, since pretreatment of cells with 4-(4-Fluorophenyl)-2-(4-methylsulfinylphenyl)-5-(4-pyridyl)-1H-imidazole, a specific inhibitor of CSBP, blocks the activation of MAPKAP kinase-2. In turn, MAPKAP kinase-2 phosphorylates the small heat shock proteins HSP25/27 in vitro and in vivo (Rouse et al., supra; Freshney et al., supra and Cuenda et al., supra). Inhibitors of CSBP also block the production of inflammatory cytokines from LPS stimulated human monocytes (Lee et al., supra) and IL-1 stimulated endothelial cells (Lee, et al.,, (1993) Ann N. Y. Acad. Sci. 696, 149–170), and more recently CSBP has been implicated in the apoptosis of neurons upon growth factor removal (Xia, et al., (1995) Science 270, 1326–1331).

Given the many signals which activate CSBP, and its potential involvement in several cellular responses, it is of interest to discover further activators and substrates. As disclosed herein, human CSBP was used as the bait in a yeast two-hybrid screen.(Fields, et al., (1989) Nature 340, 245–247) to identify a serine-threonine protein kinase, MAPKAP kinase-3, which binds to and is an in vivo and in vitro substrate of CSBP. This kinase was disclosed by Sithanandam, G. et al., in "Tyrosine Phosphorylation and Cell Signaling" (Abst) Cold Spring Harbor Laboratory, Cold Spring Harbor, N.Y., May 3–7, 1995, page 172 and in Mol. Cellular Biol, 16(3): 868–76 (1996).

The DNAs of this invention, such as the specific sequences disclosed herein, are useful in that they encode the genetic information required for the expression of the novel MAPKAP kinases. Additionally, the sequences may be used as probes in order to isolate and identify any additional members of the MAPKAP kinase family as well as forming the basis of antisense therapy for disease conditions which are characterized by atypical expression or activation of the MAPKAP kinase genes. The novel protein itself is useful directly as a diagnostic agent as well as a component in a screening system for compounds which are antagonists or agonists of effector activity. The protein is also useful for eliciting antibody production in heterologous species, said antibodies being useful for the aforesaid diagnostic, therapeutic and screening applications. These and additional uses for the reagents described herein will become apparent to those of ordinary skill in the art upon reading this specification.

BRIEF DESCRIPTION OF THE INVENTION

This invention provides isolated nucleic acid molecules encoding a MAPKAP kinase-3, including mRNAs, DNAS, cDNAs as well as antisense analogs thereof and biologically active and diagnostically or therapeutically useful fragments thereof.

This invention also provides recombinant vectors, such as cloning and expression plasmids useful as reagents in the recombinant production of MAPKAP kinases or peptides, as well as recombinant prokaryotic and/or eukaryotic host cells comprising MAPKAP kinase encoding nucleic acid sequences.

This invention also provides methods of identifying ligands (e.g., interacting proteins or substrates) capable of binding to MAPKAP kinase by measuring the binding of the ligand to be identified relative to known ligands.

This invention also provides methods for screening drugs to identify compounds which interact with and bind to the MAPKAP kinase and/or CSBP. The protein may be in isolated form in solution, or in immobilized form, or may be genetically engineered to be expressed on the surface of recombinant host cells such as in phage display system or as fusion proteins. Alternatively, whole cells or cytosolic fractions comprising MAPKAP kinase and CSBP may be employed in screening protocols. Regardless of the form of the protein, a plurality of compounds are contacted with the kinase and the binding protein under conditions sufficient to form a compound/binding protein/kinase complex and compound capable of forming, enhancing or interfering with said complexes are detected.

This invention also provides nucleic acid probes comprising nucleic acid molecules of sufficient length to specifically hybridize to MAPKAP kinase-like sequences.

This invention also provides for an antisense oligonucleotide having a sequence capable of binding with mRNAs encoding MAPKAP kinases so as to prevent the expression or translation of said mRNA. Preferably, this oligonucleotide sequence is all or part of the complementary sequence of Sequence ID. No: 1, preferably being a polynucleotide of about 10 to about 100 nucleotide residues, more preferably from about 50 to about 80 nucleotide residues, and most preferably from about 20 to about 40 nucleotides. Also preferred are antisense oligonucleotides comprising the ribosome binding site, start codon or stop codon of the complementarly strand of the oligonucleotides of Sequence ID No. 1. Antisense oligonucleotides to MAPKAP kinase (particularly MAPKAP-2 and MAPKAP-3) gene expression control elements, including but not limited to a polyadenylation region, splice sites, and promoter are also preferred.

This invention also provides transgenic non-human animals comprising or lacking a nucleic acid molecule encoding a MAPKAP kinase. Also provided are methods for use of said transgenic animals as models for differential expression of MAPKAP kinase, mutation and SAR evaluation as well as in ligand and drug screens.

This invention also provides fusion proteins comprising a MAPKAP binding domain and a binding protein ligand binding indicator domain capable of providing an analytically detectable signal. Also provided are methods of screening drugs by forming, enhancing or interfering with the detectable signal.

This invention also provides method of screening compounds to identify those compounds which bind to a MAPKAP protein comprising: providing a recombinant host cell expressing on the surface thereof a MAPKAP protein, said protein being associated with a second component capable of providing a detectable signal in response to the binding of a compound to said protein; contacting a plurality of candidate compounds with said host cells under conditions sufficient to permit binding of compounds to the binding protein; and identifying those compounds capable of binding by detecting the signal produced by said second component.

BRIEF DESCRIPTION OF THE FIGURES

FIG. 1 illustrates the sequence and alignment of human MAPKAP kinases-2 (SEQ ID NO:3 and 4) and -3 (SEQ ID NO:2). The predicted amino acid sequence of MAPKAP kinase-3 and alignment with MAPKAP kinase-2A (SEE ID NO:3) (Stokoe, et al., (1993) *Biochem. J.* 296, 843–849) and MAPKAP kinase-2B (SEQ ID NO:4) (Zu, et al., (1994) *Biochem. Biophys. Res. Commun.* 200, 1118–1124). The alignment was performed using MEGALIGN (DNASTAR, Inc.). The human MAPKAP kinase-3 cDNA sequence (SEQ ID NO:1) has been deposited in GenBank (Accession No. U43784). Roman numerals indicate various kinase subdomains (Hanks et al., supra). The proline rich motif in the N terminus and the putative nuclear localization signal at the C terminus are boxed. Residues phosphorylated by CSBP/p38 in MAPKAP kinase-2, as well as the autophosphorylation sites. (Ben-Levy, R., Leighton, I. A., Doza, Y. N., Attwood, P., Morrice, N., Marshall, C. J. and Cohen, P. (1995) *EMBO J.* 14, In Press) are shown by an asterisk and a dot, respectively, below the sequence.

FIGS. 2A–2C illustrate that GST-MAPKAP kinase-3 binds CSBP from COS and HeLa cells. A, GST or GST-MAPKAP kinase-3 (5 μg) loaded Sepharose beads (20 μl) were mixed with COS cell lysates (100 μg) expressing FLAG-tagged CSBP1, CSBP2 or CSBP2(D168A) respectively. After incubation for 2 hours at 4° C., beads were pelleted and washed extensively with lysis buffer and analyzed by immunoblotting with anti-FLAG antibody. Lane 7 (labeled "C") represents a control COS cell lysate expressing CSBP immunoprecipitated with anti-CSBP. The same experiment was also repeated with HeLa lysate (100 μg) with or without salt activation as a source of endogenous CSBP, and blotted with anti-CSBP antibody (B) or with anti-phosphotyrosine antibody (C). The position of molecular weight markers (kDa) is indicated on the left.

DETAILED DESCRIPTION OF THE INVENTION

Figure 3:
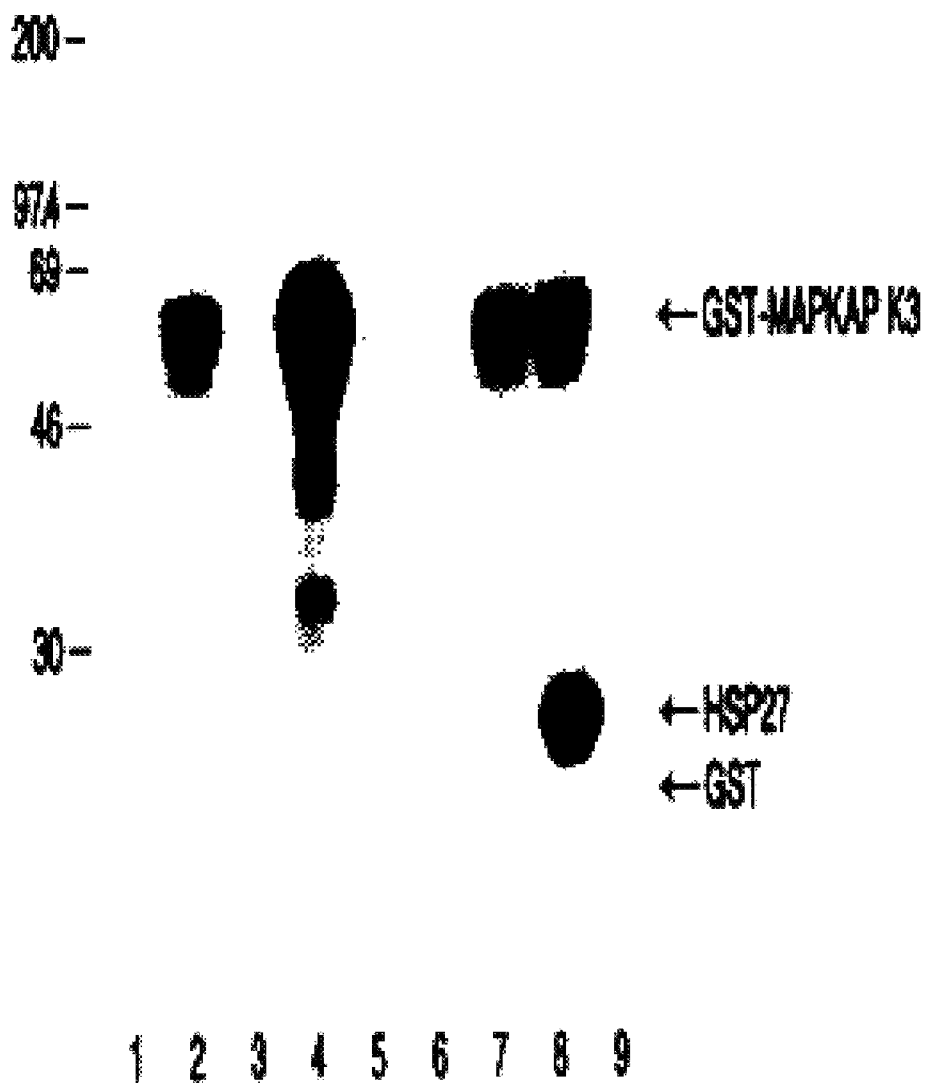
FIG. 3 illustrates that MAPKAP kinase-3 is a substrate of CSBP, and HSP27 is a substrate of MAPKAP kinase-3 in vitro. *E. coli*-expressed GST or GST-MAPKAP kinase-3 (100 μg/ml) was used a substrate in an immune-complex kinase assay with either CSBP1, CSBP2 or CSBP2 (D168A) from transfected and activated COS cells or endogenous CSBP from HeLa cells as indicated. HSP27 (120 μg/ml) was included in lanes 8 and 9 and GST-MAPKAP kinase-3 was omitted from lane 9. The position of molecular weight markers (kDa) is indicated on the left.

In further describing the present invention, the following additional terms will be employed, and are intended to be defined as indicated below.

An "antigen" refers to a molecule containing one or more epitopes that will stimulate a host's immune system to make a humoral and/or cellular antigen-specific response. The term is also used herein interchangeably with "immunogen."

The term "epitope" refers to the site on an antigen or hapten to which a specific antibody molecule binds. The term is also used herein interchangeably with "antigenic determinant" or "antigenic determinant site."

"Fusion protein" is a protein resulting from the expression of at least two operatively-linked heterologous coding sequences. The protein comprising a CSAID™ binding protein or fragment thereof and a second unrelated peptide sequence is an example of a fusion protein.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter a, in linear DNA molecules (e.g., restriction fragments) viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1) as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" or "substantially the same" when at least about 85% (preferably at least about 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., "Current Protocols in Mol. Biol." Vol. I & II, Wiley Interscience. Ausbel, et al. (ed.) (1992). Protein sequences that are substantially the same can be identified by proteolytic digestion, gel electrophoresis and microsequencing.

The term "functionally equivalent" with respect to CSBP intends that the amino acid sequence of the subject protein is one that will display the binding activity disclosed herein.

A "heterologous" region of a DNA construct is an identifiable segment of DNA within or attached to another DNA molecule that is not found in association with the other molecule in nature. Thus, when the heterologous region encodes a receptor gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation, alternative splicing or naturally occurring mutational events do not give rise to a heterologous region of DNA, as used herein.

The following abbreviations are also used herein AD, activation domain; BD, binding domain; CSBP, CSAID™ binding protein; GST, glutathione S-transferase; HA, hemagglutinin; HSP, heat shock protein; IL-1, interleukin- 1; JNK, c-Jun N-terminal kinase; MAP kinase, mitogen-activated protein kinase; MBP, myelin basic protein; MAP-KAP kinase, mitogen-activated protein kinase-activated protein kinase; PAGE, polyacrylamide gel electrophoresis; SDS; sodium dodecyl sulfate; TNF, tumor necrosis factor; UTR, untranslated region.

Because these compounds have many applications in inflammatory diseases like rheumatoid arthritis, osteoarthritis, as well as septic shock, stroke and various ischemia-reperfusion derived injuries, that compounds which block the substrate of CSBP will also have application in the same range of diseases. As shown below MAPKAP kinase-3 is an in vitro and in vivo substrate of CSBP, and that MAPKAP kinase-3 activity is stimulated by the same cell stimuli which activate CSBP activity, i.e., heat, chemical, osmotic stress, UV and the cytokines IL-1 and TNF. Hence inhibitors of MAPKAP kinase-3 activity or its activation by CSBP would have therapeutic potential much like CSAID™ compounds, but it is expected that these compounds may have unique biological properties which distinguish them from the CSAID™ compounds.

In terms of the use of MAPKAP kinase-3 as a target, this invention contemplates the following assays to screen for potential inhibitors:

1. A yeast two-hybrid screen (See: for example, U.S. Pat. No. 5,283,173) using native CSBP, splice variants, or mutants thereof such as CSBP (D168A) and MAPKAP kinase-3 fusion proteins, as configured hereinbelow, where CSBP is fused to the DNA binding domain and MAPKAP kinase-3 is fused to the activation domain. However, the assay could also be configured with CSBP fused to the activation domain and MAPKAP kinase-3 fused to the DNA binding domain. The screen is designed to recover protein-protein (enzyme-substrate) interaction antagonists. Compounds are selected based on their ability to block (or inhibit) yeast growth or β-galactosidase synthesis (Blue color) in permeabilized yeast cells (Gaber, et al., *Mol. Cell. Biol.* 9: 3447–3456 (1989)). It is appreciated that certain modification to the basic yeast dihybrid screen may be desirable, such as, substituting other DNA binding and activation domains for the those contributed by GAL-4 (e.g., lexA DNA binding domain is also contemplated for use in this invention. In addition inducible promoters can be used to drive expression in the two hybrid screens of this invention.

A yeast two-hybrid screen for CSBP (D168A)/MAPKAP kinase-3 interaction antagonist is as shown below:

A high-throughput, microtiter-formated, robotics-amenable screen based on the two-hybrid interaction (Fields and Song, 1989) between CSBP2(D168A) and MAPKAP kinase-3 and the transcriptional reporter lacZ has been configured. Briefly, the two proteins have been engineered for inducible expression (GAL1 promoter) as hybrid fusions using the interaction trap (lexA) two-hybrid system (Gyuris, et al., (1993) Cell 75:791–803). Expression plasmids have been co-introduced into yeast strain RJ501 (ade2 his3 ura3 leu2 lys2 erg6 URA3::lexAo-lacZ), and the protein-protein interaction confirmed (e.g., >100-fold induction in b-gal units in 4 h), and assay conditions established.

In the current assay format, compounds are seeded individually at some concentration (i.e. 25 ug/ml) with 2% galactose to induce protein expression and hybrid formation. Yeast cells pre-grown in selective media containing the neutral carbon source raffinose are added. The increase in beta-gal activity (Miller J. H. (1972) Experiments in Molecular Genetics (Cold Spring Harbor Laboratory, Cold Spring Harbor, N.Y.). A yeast two-hybrid screen for CSBP (D168A)/MAPKAP kinase-3 interaction antagonists) is determined following a 3–4 hour incubation. Percent inhibition is calculated, and a differential value determined with respect to a parallel control two-hybrid strain. (The control strain is the same parent yeast strain containing plasmids encoding two other proteins that are known to interact).

Modification to the above may include, but are not limited to, different yeast strains with different transcriptional reporters (i.e. auxotrophic markers like URA3), a different two-hybrid system (Fields, et al., (1989) Nature 340:245–247), and different promoters on the plasmids.

2. Inhibitors can be discovered directly in a MAPKAP kinase-3 assay in which hsp27 or peptides related to the known phosphorylation site(s) in hsp-27 are used as a substrate to measure activated MAPKAP kinase-3 activity. Inhibitors would be selected based upon their ability to reduce the amount of kinase activity as compared to control assays. For example as discussed above with respect to FIG. 3. It should be noted that a variety of kinase/protein phosphorylation assays are known in the art and may be usefully employed in connection with this invention. See for example, "Protein Phosphorylation: A Practical Approach", Hardie, D. G. (ed.) IRL Press at Oxford University Press, New York, 1993.pp300 (Particularly, Chapter 6, pgs 121–144).

The present assay includes a method for identifying a compound as a MAPKAP inhibitor comprising first obtaining purified or enriched MAPKAP kinase-3, preferably activated, i.e. phosphorylated by CSBP or a mutant form of MAPKAP kinase 3 which is constitutively active, and then incubating the kinase with a peptide or protein substrate (Clifton et al., supra) in the presence of labelled ATP, along with the inhibitor to be identified (or candidate inhibitor). One then measures the incorporation of the labelled phosphorus into the peptide or protein substrate (by methods well known in the art) for selecting an inhibitor which reduces the amount of labelled phosphorus included in the substrate.

3. Inhibitors of a binding assay between recombinant CSBP and MAPKAP kinase-3. There are many ways to configure an assay to look for compounds which inhibit the binding of MAPKAP kinase-3 to CSBP. A common screening format uses a 96-well plate in which one of the kinases, preferably purified recombinant MAPKAP kinase-3, is initially attached to the wells of an ELISA plate by overnight incubation, followed by an additional incubation with a non-specific protein such as BSA (bovine serum albumin) to block free binding sites on the plastic. Subsequently a solution containing the putative inhibitor or control buffer is added mixed with a solution containing purified recombinant CSBP and incubated for an hour or more so as to allow complete binding of CSBP to MAPKAP Kinase-3 in the control buffer well. The bound CSBP in each well is then measured. This is typically done by either labeling the CSBP with a radioactive or fluorescent label which can be detected directly, or by incubating with an additional reagent which detects the bound CSBP, such as an antibody specific for CSBP which has been fluorescently tagged or conjugated to an enzyme such as horseradish peroxidase or alkaline phosphatase, whose presence can be measured through an enzymatic reaction by providing a substrate which results in a color change. Alternatively, the CSBP could be chemically modified (conjugated) for example with biotin, and detected via the binding of fluorescent or radioactive streptavidin. Alternatively, the CSBP could be fused to a protein or peptide which has enzymatic activity, or for which there is a specific antibody for detection as described above. These and other variations to ELISA plate assays are well known to those in the art. Typically, the amount of protein used in each step and the exact combination of reagents are determined empirically. Antagonist or inhibitor compounds which block the interaction of MAPKAP kinase-3 with CSBP are those which lead to a reduced signal. The assay can also be configured with the purified recombinant CSBP attached to the well, and the MAPKAP kinase-3 is added with candidate inhibitor compound as the second step followed by detection reagents as described above for CSBP. Additional variations include attaching the MAPKAP kinase-3 or CSBP to the well through an antibody to the protein or to a protein or peptide which has been fused with the MAPKAP kinase-3 or CSBP. Only one of the components of the binding assay may need to be pure. Thus plates with MAPKAP kinase-3 attached to the wells could be incubated with cell lysates containing CSBP and binding of CSBP could be detected with antibody to CSBP or to the CSBP fusion peptide partner.

The binding of CSBP to MAPKAP kinase-3 may also established in a suitable assay format through a number of other techniques known to those skill ed in the art. For example, CSBP or MAPKAP kinase-3 could be attached to a chip, and the ending of the second kinase measured by surface plasmon resonance using an instrument such as a BIAcore. Addition of the second kinase in the presence of an inhibitor would reduce to signal seen upon addition of the second component.

Additional variations might include expressing CSBP or MAPKAP kinase-3 on the surface of a cell, and measuring the binding of a labelled (preferably radiolabelled) MAPKAP kinase-3 or CSBP respectively using radioactivity or other detection reagent.

An example of such an assay can be established in ELISA format with either or both proteins made as fusion proteins to allow suitable detection with antibodies etc. Useful epitope tags include but are not limited to Glutathione S-transferase, FLAG, or HA. See for example, the discussion with respect to FIGS. 3 and 4B. Either of the proteins may be attached to a solid support, such as glutathione or antibody coated-Beads. Such inhibitors may or may not be inhibitors of the enzymatic activity of CSBP or MAPKAP kinase-3, and all would presumably disrupt the interface between CSBP and MAPKAP kinase-3.

4. A coupled kinase assay with activated CSBP, unactivated MAPKAP kinase-3 and a peptide substrate for MAPKAP kinase-2. Inhibitors of the phosphorylation of the MAPKAP kinase-3 peptide substrate could be inhibitors of either CSBP or MAKAP kinase-3. Accordingly, an activated CSBP, isolated from *E. coli*, yeast, insect cells, mammalian cells or other suitable host cells, is mixed with unactivated wild type MAPKAP kinase or an unactivatable mutant thereof expressed in *E. coli* or other suitable host cell in the presence of a protein or peptide substrate of the MAPKAP kinase. The components should be titrated such that a test compound capable of effect either kinase activity would be detected.

In this screen, purified recombinant MAPKAP kinase-3 is mixed with a peptide substrate and suitable buffer reagents for establishing a kinase assay (see Clifton et al., FEBS Lett. 392:209–214 (1996)). At this stage the MAPKAP kinase-3 should be in an inactive state. Such would be the case if the protein is expressed in *E. coli* or in unstimulated insect or mammalian cells, such that the protein is unphosphorylated. Candidate inhibitor or control solution is then added followed by an active, phosphorylated form of CSBP, as might be obtained from expression in yeast or mammalian cells treated as has been previously described (Lee et al., Nature 372:739–746 (1994); Kumar et al., J. Biol. Chem. 270:29043 (1966); Cuenda et al., FEBS Lett. 364:229–233 (1995)). The phosphorylation of the MAPKAP kinase-3 peptide substrate is then measured as in the described assay (Clifton et al., FEBS Lett. 392:209–214 (1996)) or by variants such as attaching the peptide substrate to a bead which allows detection by scintillation proximity (known in the art as SPA). Other variations of kinase assays are known to those in the art. The screen looks for compounds which reduce the phosphorylation of the MAPKAP kinase-3 peptide substrate. Depending on the exact amounts of each kinase and substrate in the mixture, this assay will detect compounds which inhibit the association of CSBP with MAPKAP kinase-3, compounds which inhibit the activation, i.e., phosphorylation, of MAPKAP kinase-3 by CSBP, and those compounds which inhibit the kinase activity of MAPKAP Kinase-3.

Central to the development of these assays is the isolation of an intermediate in the kinase cascade. One such useful protein is MAPKAP kinase-3 and its isolation and characterization is given below.

The present assay includes a method for identifying a compound as a MAPKAP inhibitor comprising first obtaining unactivated MAPKAP kinase-3 and CSBP, and then incubating the kinase with a peptide or protein substrate (Clifton et al., supra) in the presence of labelled ATP, along with the inhibitor to be identified (or candidate inhibitor). One then measures the incorporation of the labelled phosphorus into the peptide or protein substrate (by methods well known in the art) for selecting an inhibitor which reduces the amount of labelled phosphorus included in the substrate. Preferably the MAPKAP Kinase 3 and CSBP are purified. Suitably, the MAPKAP Kinase-3 is expressed as a fusion protein in E. Coli and the CSBP is expressed as a fusion protein in yeast.

EXPERIMENTAL PROCEDURES

Cell Culture and Transfection—COS and HeLa cells were maintained in DMEM supplemented with 10% fetal bovine serum (Life Technologies, Inc.) in a humidified 5% $CO_2$ environment. Transient transfections were performed using Lipofectamine reagent according to the manufacturer's recommendations (LTI).

Plasmid Construction for Two-Hybrid and Mammalian Expression—Plasmids pGBT9, pGAD424, pTD1, pVA3, and pLAM5' were purchased from Clontech Laboratories. Plasmid pTD1 encodes a GAL-4-SV40 large T-antigen fusion protein (in pGAD3F) and pVA3 encodes a GAL4-BD-p53 fusion protein (in pGBT9). These proteins were used as a positive control in the two-hybrid assay.(Li, et al., (1993). FASEB J. 7, 957–963; Iwabuchi, et al., (1993). Oncogene 8, 1693–1696). pLAM5' encodes a GAL4-BD-lamin C fusion protein and was used to eliminate false positives. The 1.2-kb XhoI-Asp718I fragment from pl37NBU-CSBP2 .(Kumar et al., supra) was blunt end cloned into the SmaI site of pGBT 10 (E. Rheaume, personal communication) to create pGBT10-CSBP2. (pGBT10 is a modification of pGBT9.(Bartel et al., (1993). Oxford. 153–179) where the SmaI site is in the +1 position when compared to its position in pGBT9.) The in-frame fusion of pGBT10CSBP2 was confirmed by sequencing on an automated DNA sequencer (Applied Biosystems, Inc.). Replacement of the 904-bp BglII fragment from pGBT10-CSBP2 with the 886-bp BglII fragment from p138NBU-CSBP2 (D168A). (Kumar et al., supra) created PGBT10-CSBP2 (D168A). Mammalian vectors for expressing epitope tagged CSBP cDNAs were engineered by PCR amplifying the coding sequence of CSBP1, CSBP2 and CSBP2 (D168A) using a 5' primer encoding the FLAG epitope (International Biotechnology, Inc.) and a 3' primer from pBS-CSBP (Kumar et al., supra) and subcloned into CDN (Kumar, et al., (1995) J. Biol. Chem. 270, 27905–27913). Similarly, a mammalian expression vector encoding hemagglutinin (HA—12CA5).( Wilson, et al., (1984). Cell 37, 767–778) epitope-tagged MAPKAP kinase-3 was constructed by PCR using a 5' primer encoding the HA epitope. The transient expression of epitope-tagged proteins in both COS and HeLa cells was confirmed by immunoblotting with anti-HA (Boehringer Manheim) and anti-FLAG (IBI) or anti-CSBP antiserum (Freshney et al., supra).

Yeast Two-Hybrid Screen—A GAL4-AD/human leukocyte cDNA fusion library was purchased from Clontech. Transformations of HF7c (MATa, ura3-52, his3-200, lys2-801, ade2-101, trpl-901, leu2-3,112, gal4-542, gal80-538, LYS2::GAL1-HIS3, URA3::(GAL4 17-mers)$_3$-CYCl-lacZ) .( Feilotter, et al., (1994). Nucleic Acids Res. 22, 1502–1503) were performed by a modification of the lithium acetate method as recommended by Clontech. Expression of stable fusion proteins from both CSBP constructs was detected with a rabbit polyclonal antiserum to the DNA-binding domain (BD) of yeast GALA (Upstate Biotechnologies, Inc.). Selection of library proteins interacting with CSBP2 (D168A) was carried out on synthetic complete (SC) media lacking tryptophan, leucine and histidine (SC-Trp-Leu-His) and containing 10 mM 3-aminotriazole (Sigma Chemical Co.). Colony lift β-galactosidase filter assays were performed as recommended by Clontech. Plasmid pCL1 (encoding MAPKAP kinase-3) was rescued from yeast by electroporation of DH5α and sequenced as above.

Expression of MAPKAP Kinase-3 as a GST Fusion Protein—The 1.39-kb EcoRI insert from pCL1 was ligated to EcoRi-digested pGEX-SX-1 (Pharmacia Biotechnology, Inc.). The resulting plasmid pGEX-5X-CL1 was introduced into Escherichia coli strain BL21 (Pharmacia). Cells were cultured at 30° C. in 2X YTA (16g/l yeast extract. 5g/l NaCl. 100 ug/ml ampicillin) and the expression of protein was induced by the addition of 0.1 mM isopropyl-β-D-thiogalactosidase for 2h. The glutathione S-transferase (GST) or GST-MAPKAP kinase-3 fusion protein was purified by glutathione-sepharose (GSH-sepharose) affinity chromatography according to vendor's directions. The integrity and purity of the 67-kDa GST-MAPKAP kinase-3 was determined to be >95% as judged by SDS-PAGE and Coomassie staining.

Immunoprecipitation and Kinase Assay—Mammalian cells expressing epitope-tagged proteins were activated with 0.4 M sorbitol or 20 ng/ml TNF treatment. In some cases cells were pretreated with 10 μM 4-(4-Fluorophenyl)-2-(4-methylsulfinylphenyl)-5-(4-pyridyl)-1H-imidazole. (Lee et al., (1994). Nature 372, 739–746; and Cuenda et al., supra). The cells were washed twice in PBS and solubilized on ice in lysis buffer (20 mM Tris-HCl pH 7.4, 150 mM NaCl, 1% Triton X-100, 10% glycerol, 2 mM EDTA, 25 mM β-glycerophosphate, 20 mM NaF, 1 mM sodium orthovanadate, 2 mM sodium pyrophosphate, 1 mM phenylmethylsulfonyl fluoride, 1 μg/ml leupeptin, 5 U/ml aprotinin) and centrifuged at15,000 X g for 20 min at 4° C. Endogenous or epitope-tagged (FLAG for CSBP and HA for MAPKAP kinase-3) proteins were precipitated from cell lysates using appropriate antibodies for 2 hours at 4° C. The beads were washed twice with lysis buffer and twice with kinase buffer (25 mM Hepes pH 7.4, 25 mM $MgCl_2$, 25 mM β-glycerophosphate, 100 μM sodium orthovanadate, 2 mM DTT) and the immune-complex kinase assays were initiated by the addition of 25 μof kinase buffer containing 1–5 μg of substrate and 50 μM [γ-$^{32}$p] ATP (20 Ci/mmol). After 30 min at 30° C. the reaction was stopped by the addition of SDS sample buffer and the phosphorylated products analyzed by SDS-PAGE and autoradiography.

Binding of Endogenous CSBP or FLAG-CSBPs to GST—or HA-MAPKAP Kinase-3—GST-MAPKAP kinase-3 bound to GSH-sepharose (~5 μg protein/20 μl beads) was incubated at 4° C. for 2 h with gentle rotation with either sorbitol-stimulated COS cell (expressing epitope-tagged CSBP1, CSBP2 or CSBP2(D168A)) or HeLa cell lysates (100 μg) with and without sorbitol stimulation (expressing endogenous CSBP). The beads were washed 6 times with 1 ml of lysis buffer and CSBP protein bound to beads was detected by immunoblotting with anti-FLAG (IBI) or anti-CSBP specific antiserum.(Lee et al., (1994). Nature 372,739–746). For co-precipitation studies in vivo, HA-tagged MAPKAP kinase-3 and FLAG-tagged CSBP2 were co-transfected into HeLa cells. Cell lysates were immunoprecipitated with anti-HA antibody (Boehringer Manheim) and immunoblotted with anti-FLAG antibody to detect co-precipitated FLAG-CSBP.

RESULTS AND DISCUSSION

Cloning of a cDNA Encoding a Protein Interacting with CSBP—A yeast two-hybrid screen was used to identify proteins that interact with CSBP. When full-length length wild-type CSBP2 was constructed as a GALA-BD fusion, it activated the HIS3 reporter in HF7c in the absence of an interacting protein. Since CSBP2 expressed in yeast is active in the absence of an exogenous stimulus. (Kumar et al., (1995). *J. Biol. Chem.* 270, 29043–29046), it was suspected that this activation may have been related to the high basal kinase activity. Therefore, a catalytically inactive form of the enzyme, CSBP2(D168A) (Kumar et al., supra), was engineered as a GAL4-BD fusion, and this did not activate the HF7c HIS3 reporter when co-transformed with the GAL4-AD plasmid. This GALA-BD-CSBP2 (D168A)-encoding plasmid was transformed with a GAL4-AD-human leukocyte cDNA fusion library into HF7c and the transformants plated on SC-Trp-leu-His media to directly select for cells containing both plasmids as well as for interacting two-hybrid proteins. A total of 87 positives were obtained from this primary screen, but only one strain tested positive for activation of both reporter genes (i.e., $His^+$ and blue color for $lacZ^+$). The GAL4-AD library plasmid isolated from this strain, pCL1 (for CSBP, Leukocyte 1) was retransformed into HF7c in the presence of either control or the GAL4-BD-CSBP(D168A)-encoding plasmids. Activation of the HIS3 and lacZ reporters occurred only when pCL1 was present in combination with the plasmid encoding GAIA-BD-CSBP2(D168A) but not with the control plasmids encoding GAL4-BD or GAL4-BD-human lamin C fusion protein.

Analysis of Predicted CSBP Interacting Protein Sequence—Upon sequencing, a possible initiation codon, following the predictions of Kozak. (Kozak, M. (1986). *Cell* 44, 283–292), was found at the 14th codon following the 5' EcoRI site, and this was followed by an complete open reading frame encoding a 382-amino acid protein with a calculated $M_r$ of 42.8 kDa. A search of GENBANK indicated that the pCL1-encoded protein was novel and closely related to the serine-threonine protein kinase MAPKAP kinase-2. The predicted amino acid sequence of the 1.39 kb pCL1 cDNA insert and its alignment with the two known isoforms of human MAPKAP kinase-2 are shown in FIG. 1. Because it shares ~70% amino acid identity with the two known isoforms of human MAPKAP kinase-2 and 31% amino acid identity with another MAP kinase substrate, $p90^{rsk}$ (also known as MAPKAP kinase-1) this new protein is designated MAPKAP kinase-3. Interestingly, MAPKAP kinase-3 does not appear to retain the Pro-Pro-Pro-Xaa-Pro-Pro sequence found in the N-terminal domain of MAPKAP kinase-2 which has been suggested to be a binding site for SH3 domains. (Stokoe, et al., (1993). *Biochem. J.* 296, 843–849), but it does nearly retain the putative nuclear localization signal found near the C terminus of one of the two MAPKAP kinase-2 splice variants.

Northern blot analysis showed a predominant mRNA of 3.5 kb and minor mRNA of 2 kb in most tissues except brain, with highest abundance in heart and skeletal muscle (data not shown).

In Vitro Association of MAPKAP Kinase-3 with CSBP—The identification of MAPKAP kinase-3 through its interaction with CSBP2 in a yeast two-hybrid screen suggested that it should bind CSBP in vitro. This was confirmed by incubating bacterially-expressed and purified GST-MAPKAP kinase-3 with COS cell lysates expressing transfected CSBP1, CSBP2, CSBP2(D168A) or HeLa cell lysate expressing the endogenous CSBP (FIG. 2A) followed by precipitation and analysis by SDS-PAGE and immunoblot. GST-MAPKAP kinase-3 was able to bind and precipitate all three CSBPs from COS cells and endogenous CSBP from HeLa cells, indicating that both spliced forms of CSBP bind to MAPKAP kinase-3 independent of kinase activity. The lower amount of CSBP1 associated with GST-MAPKAP kinase-3 was due to a lower expression of CSBP1 in transfected COS cells (data not shown). After compensation for the expression level, the binding efficiencies for CSBP1, CSBP2 and CSBP2(D168A) are comparable. Also shown was that activated epitope-tagged CSBP1. CSBP2, and CSBP2(D168A) isolated from transfected COS cells could precipitate GALA-AD-MAPKAP kinase-3 but not GAL-AD alone from yeast lysates (data not shown).

The presence of small amounts of a slower migrating form of CSBP in precipitates (e.g., FIG. 2A) which corresponds to the activated, tyrosine phosphorylated form of the enzyme, suggests that both activated and unactivated forms of CSBP can bind. This was further demonstrated by the experiments illustrated in FIGS. 2B and 2C, where GST-MAPKAP kinase-3 bound and precipitated both tyrosine phosphorylated and non-tyrosine phosphorylated CSBP from HeLa cells treated with or without sorbitol. In additional experiments, it was shown that purified recombinant CSBP binds to purified GST-MAPKAP kinase-3 indicating that the association is direct and does not depend on any other proteins present in the yeast or mammalian cell lysates.

MAPKAP Kinase-3 is an In Vitro Substrate of CSBP, and HSP27 is an In Vitro Substrate of MAPKAP Kinase-3—MAPKAP kinase-3 was tested to see if it could act as a substrate of CSBPs by performing immune-complex kinase assays with activated CSBPs and either GST-MAPKAP kinase-3 or control GST. Both CSBP1 and CSBP2 from transfected COS cells and endogenous CSBP from HeLa cells phosphorylated GST-MAPKAP kinase-3 but not GST (FIG. 3, lanes 1–4, 7) indicating that MAPKAP kinase-3 is indeed a substrate of CSBP. In contrast, the catalytically inactive CSBP2(D168A) did not show any phosphorylation of GST-MAPKAP kinase-3 (FIG. 3, lane 6). As in the co-precipitation experiments, the differences in kinase activity between COS-expressed CSBP1, CSBP2 and endogenous HeLa CSBP are most likely due to the varying level of CSBP expression. Indeed, any differences in substrate preference between CSBP1 or CSBP2 have yet to be found.

Since Hsp27 is a known substrate of MAPKAP kinase-2 in vitro and in vivo, it was determine it was also a substrate of MAPKAP kinase-3. Inclusion of HSP27 in the CSBP/GST-MAPKAP kinase-3 immune-complex kinase reaction resulted in its phosphorylation (FIG. 3, lane 8) whereas CSBP alone or unactivated MAPKAP kinase-3 did not phosphorylate Hsp27 (FIG. 3, lane 9 and data not shown) indicating that Hsp27 is a substrate of MAPKAP kinase-3.

Figure 4:
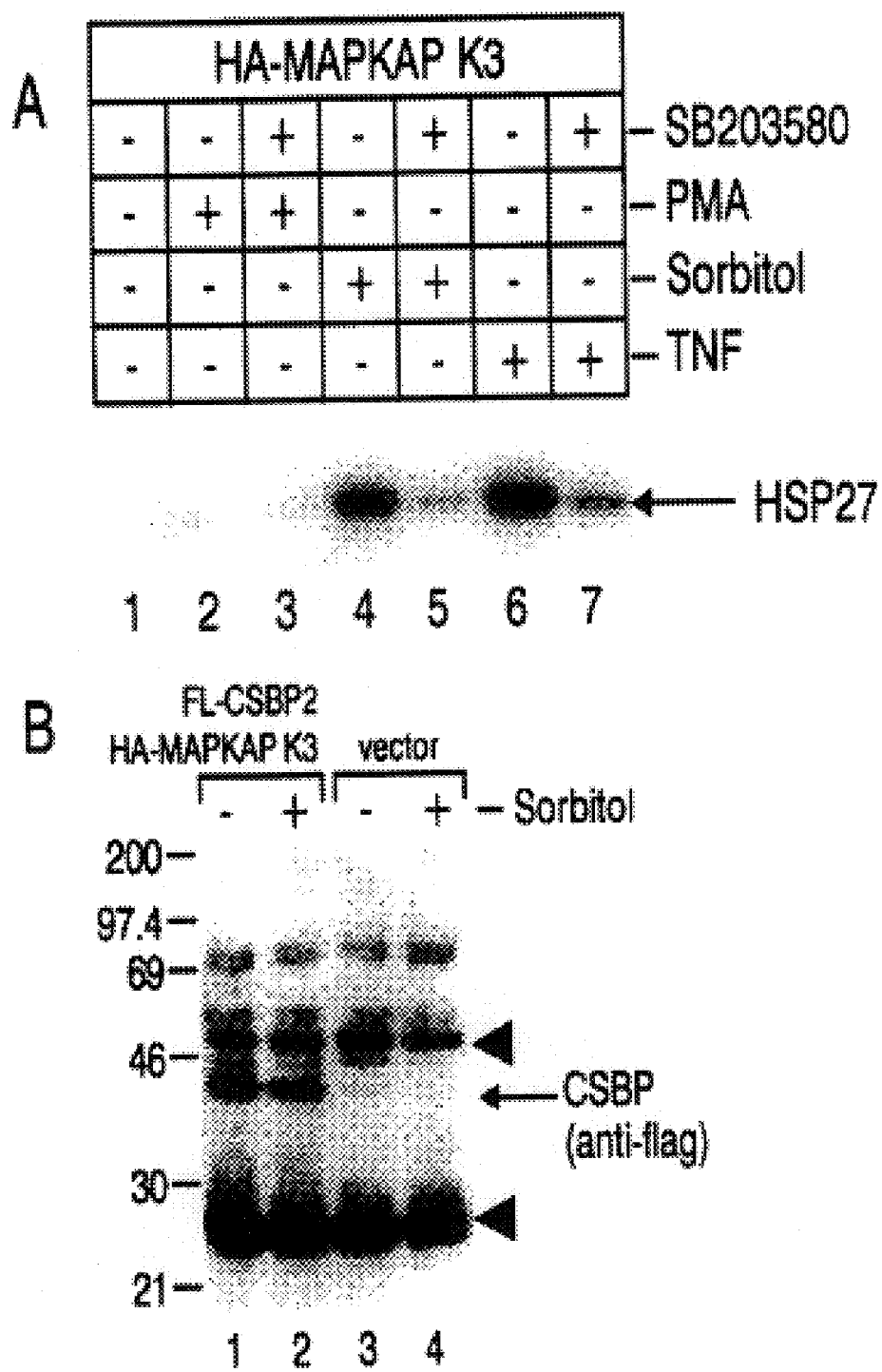
FIGS. 4A and 4B illustrate that sorbitol- and TNF-mediated cell stimulation results in CSBP and MAPKAP kinase-3 activation. A, HeLa cells were either transfected with vector alone (lanes 1–3) or with HA-tagged MAPKAP kinase-3 (lanes 4–8) and pretreated with 10 μM 4-(4-Fluorophenyl)-2-(4-methylsulfinylphenyl)-5-(4-pyridyl)-1H-imidazole and/or treated with 0.4 M sorbitol or 20 ng/ml TNF for 10 min as indicated. After activation, the cells were lysed and HA-MAPKAP kinase-3' was immunoprecipitated with anti-HA antibody and an immune-complex kinase assay was performed with HSP27 as a substrate (indicated by an arrow). B, HeLa cells were either co-transfected with FLAG-CSBP2 and HA-MAPKAP kinase-3 (lanes 1 and 2) or with vector alone (lanes 3 and 4) activated with 0.4 M sorbitol for 10 min, and immunoprecipitated with anti-HA antibody. The immunoprecipitate was analyzed by immunoblot using anti-FLAG antibody to detect co-precipitated FLAG-CSBP (indicated by an arrow). Arrow heads indicate the heavy and light chain of anti-HA antibody used for immunoprecipitation.

MAPKAP Kinase-3 Associates with and is a Substrate of CSBP In Vivo—To determine if stress and cytokine activation of the CSBP pathway leads to MAPKAP kinase-3 activation, HeLa cells were transfected with either plasmid vector alone or vector expressing HA-tagged MAPKAP kinase-3 and treated them with sorbitol or TNF in the presence of absence of 4-(4-Fluorophenyl)-2-(4-methylsulfinylphenyl)-5-(4-pyridyl)-1H-imidazole, a specific inhibitor of CSBP kinase activity (7, 16). MAPKAP kinase-3 was isolated from these cells using anti-HA antibodies and an immune-complex kinase assay was performed with HSP27 as a substrate. As shown in FIG. 4A, both sorbitol and TNF treatment stimulated MAPKAP kinase-3 activity (FIG. 4A, lanes 4, 5 and 7) which was almost completely blocked by pretreatment with 10 $\mu$M 4-(4-Fluorophenyl)-2-(4-methylsulfinylphenyl)-5-(4-pyridyl)-1H-imidazole (FIG. 4A, lanes 6 and 8). Cells transfected with the vector alone, and processed similarly, did not have any MAPKAP kinase-3 activity (FIG. 4A, lanes 1–3). These results suggest that stress- and cytokine-activated CSBP activates MAPKAP kinase-3 in vivo.

To confirm the association of CSBP and MAPKAP kinase-3 in vivo, FLAG-tagged CSBP2 and HA-tagged MAPKAP kinase-3 were coexpressed in HeLa cells. Immunoprecipitation of MAPKAP kinase-3 with anti-HA antibody resulted in co-precipitation of CSBP in cells transfected with both cDNAs but not from cells transfected with vector alone, as determined by immunoblotting with anti-FLAG antibodies (FIG. 4B, lanes 1–4). Like the data in FIG. 2B, the amount of CSBP co-precipitated from sorbitol-activated cells was lower than that from unactivated cells, suggesting weaker association of the CSBP-MAPKAP kinase-3 complex. These data indicate that MAPKAP kinase-3 is functionally similar to MAPKAP kinase-2, in that they are both in vivo substrates of CSBP/p38, and can phosphorylate Hsp27 in vitro. It is not clear whether both kinases contribute to phosphorylation of hsp27 in vivo.

The finding of association between CSBP and its substrate MAPKAP kinase-3 is reminiscent of that between ERK2 and p90$^{rsk}$ (also known as MAPKAP kinase-1)(Hsiao, et al., (1994). Proc. Natl. Acad. Sci. USA 91, 5480–5484), in which the two kinases were found to be in a stable 110-kDa complex within unactivated Xenopus oocytes. Upon activation, ERK dissociates from the complex and is predominantly monomeric. Similarly, in the present case a stable complex between CSBP and MAPKAP kinase-3 exists in vivo, and the preliminary data in FIGS. 2B and 4B suggest some dissociation of the activated enzymes, although further experiments will be needed to establish this.

There are several reports of MAP kinases binding to other proteins. ERK has been reported to interact with the transcription factor Elk1 (Rao, et al., (1994). *Oncogene* 9, 1855–1860;and Zinck, et al., (1993). EMBO J. 12, 2377–2387) and the high and low affinity NGF receptors. (Volonte, et al., (1993). *J. Biol. Chem.* 266, 21410–21415) by co-immunoprecipitation from mammalian cells, and the protein kinase MEK1 in a yeast two-hybrid screen,(Xu, et al., (1995). *Proc. Natl. Acad. Sci. USA* 92, 6808–6812). JNK binds to the transcription factors c-Jun and ATF2 in vitro (Gupta, et al., supra). Formation of these complexes may serve to restrict cross-talk between different MAP kinase pathways. For example, both ERK and CSBP can activate MAPKAP kinase-2 in vitro but only CSBP appears to activate MAPKAP kinase-2 in vivo. (Rouse et al., supra; Stokoe, et al., supra; and, Ben-Levy, et al., (1995). EMBO J. 14, In Press). Similarly, ERK phosphorylated MAPKAP kinase-3 in vitro, but the activation of cells with phorbol esters (a potent activator of this MAP kinase pathway) did not result in the activation of transfected MAPKAP kinase-3. JNK, another stress- and cytokine-activated MAP kinase, did not phosphorylate MAPKAP kinase-3 in vitro. Thus, MAPKAP kinase-3 appears to be a specific substrate of CSBP.

Recently, the sites of MAPKAP kinase-2 phosphorylation by CSBP/RK in vitro and in vivo were determined.(Ben-Levy et al., supra) and are illustrated in FIG. 1. The three key phosphorylation sites, Thr222, Ser272 and Thr334, any two of which must be phosphorylated for maximal activation of MAPKAP kinase-2 activity, are conserved in MAPKAP kinase-3. An additional in vivo autophosphorylation site is also conserved (Thr338) while a second site is changed from Ser to Thr (Ser9) and a third is not conserved (Thr25). Another component of MAPKAP kinase-2 activation conserved in MAPKAP kinase-3 is an autoinhibitory alpha-helix near the C terminus, which mimics the substrate and when deleted produces a constitutively active MAPKAP kinase-2 (Engel, et al., (1995). *J. Biol. Chem.* 270, 27213–27221). Thus, the conserved features appear to play a role in the activation of MAPKAP kinase-3.

Given the apparent similarity in activation and substrate activity of MAPKAP kinase-2 and MAPKAP kinase-3, either may be used as a target in the screens identified above. The availability of purified CSBP and MAPKAP kinase-3 and their cDNAs permit the employment of the screens mentioned above.

In addition to the methods of expression given above, the proteins of this invention can be made by a variety of recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial) or eukaryotic (e.g., yeast or mammalian) cells by methods well known in the art (Ausubel et al. supra). The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ(*E. coli*) pBR322 (*E. coli*) pACYC177 (*E. coli*) pKT230 (gram-negative bacteria) pGV1106 (gram-negative bacteria) pLAFR1 (gram-negative bacteria) pME290 (non-*E. coli* gram-negative bacteria) pHV14 (*E. coli* and *Bacillus subtilis*) pBD9 (Bacillus) pIJ61 (Streptomyces) pUC6 (Streptomyces) YIp5 (Saccharomyces) a baculovirus insect cell system,, YCp19 (Saccharomyces). See, generally, "DNA Cloning": Vols. I & II, Glover et al., eds. IRL Press Oxford (1985) (1987) and; T. Maniatis et al. "Molecular Cloning", Cold Spring Harbor Laboratory (1982).

The gene can be placed under the control of a promoter, ribosome binding site (for bacterial expression) and, optionally, an operator (collectively referred to herein as "control" elements) so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. Alternatively, gene fusions may be created whereby the gene encoding the binding protein of interested is fused to a gene encoding a product with other desirable properties. For example, a fusion partner could provide known assayable activity (e.g. enzymatic) which could be used as an alternative means of selecting the binding protein. The fusion partner could be a structural element, such as a cell surface element such that the binding protein (a normally cytosolic component) could be displayed on the cell surface in the form of a fusion protein. It may also be desirable to produce mutants or analogs of the protein of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis and the formation of fusion proteins, are well known to those skilled in the art. See, e.g., T. Maniatis et al., supra; *DNA Cloning*, Vols. I and II, supra; *Nucleic Acid Hybdridization*, supra.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1neo, a vector derived from pCDNA1(*Mol. Cell Biol.* 7:4125–29) which uses the CMV promoter to drive expression. Both these latter two vectors can be employed for transient or stable(e.g. using G418 or hygromycin resistance) expression in mammalian cells. Insect cell expression systems, e.g., Drosophila, are also useful, see for example, PCT applications US 89/05155 and US 91/06838 as well as EP application 88/304093.3 and Baculovirus expression systems.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired binding protein.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not particularly preferred.

The binding proteins of the present invention or their fragments comprising at least one epitope can be used to produce antibodies, both polyclonal and monoclonal. If polyclonal antibodies are desired, a selected manmal, (e.g., mouse, rabbit, goat, horse, etc.) is immunized with a binding protein of the present invention, or its fragment, or a mutated binding protein. Serum from the immunized animal is collected and treated according to known procedures. When serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e., M. Schreier et al., "Hybridoma Techniques" (1980); Hammerling et al., "Monoclonal Antibodies and T-cell Hybridomas" (1981); Kennett et al., "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the protein of interest, or fragment thereof, can be screened for various properties; i.e., for isotype, epitope, affinity, etc. Alternatively, genes encoding the monoclonals of interest may be isolated from the hybridomas by PCR techniques known in the art and cloned and expressed in the appropriate vectors. Monoclonal antibodies are useful in purification, using immunoaffinity techniques, of the individual proteins against which they are directed. The antibodies of this invention, whether polyclonal or monoclonal have additional utility in that they may be employed reagents in immunoassays, RIA, ELISA, and the like. In addition they can be used to isolate the MAPKAP kinases from human cells and determine the effect of different stimuli and compounds on the phosphorylation state and protein kinase activity of endogenous MAPKAP kinase. The antibodies could be used to establish a tissue culture based assay for discovery or modification of novel compounds which block the phosphorylation or kinase activity of MAPKAP kinase. An example of such an assay would be to incubate human monocytes or monocytic cell lines with a compound or compound mixture prior to treatment with LPS for a defined time period, followed by immunoprecipitation of MAPKAP kinase with antibody and assessment of its phosphorylation state via immunoblot or chromatography or measurement of its kinase activity with appropriate protein or peptide substrate. Appropriate peptide substrates for use in the present invention may be found in Clifton et al., FEBS Lett., Col 392, 209–214 (1996) whose disclosure is incorporated herein by reference in its entirety.

This invention provides a method for determining whether a ligand previously not known to bind to a MAP- KAP kinase can bind to such a protein. The method comprises contacting the ligand to be identified with cytosolic fraction from MAPKAP kinase producing cells and measuring its ability to compete with a known radioactive MAPKAP kinase substrate, as described above, in the ligand binding assay. Alternative methods include contacting the ligand to be identified with a whole-cell expressing the coding sequence of a MAPKAP kinase under conditions sufficient for binding of ligands previously identified as binding to such a receptor. In other embodiments cell membrane fractions comprising the MAPKAP kinase fusions or isolated MAPKAP kinase free or immobilized on solid supports may be used to measure binding of the ligand to be tested. When recombinant cells are used for purposes of expression of the MAPKAP kinase it is preferred to use cells with little or no endogenous MAPKAP kinase activity so that binding if any is due to the presence of the expressed protein of interest. As mentioned previously, a specifically designed indicator of receptor binding can be constructed. For example a fusion protein can be made by fusing the MAKAP kinase of this invention with a protein domain which is sensitive to MAPKAP kinase/ligand binding. Such a domain referred to here as an indicator domain is capable, itself, or in association with accessory molecules, of generating an analytically detectable signal which is indicative of receptor ligand binding. A variation of this approach is to express MAPKAP kinase as a fusion protein (e.g., fused to FLAG peptide) in THP.1 or other mammalian cells, and to use the fusion peptide as a means of isolating the recombinant MAPKAP kinase after suitable stimulation and pretreatment of the cells. Such expression can be achieved with numerous mammalian expression vectors which utilize viral promoters, e.g., CMV, RSV and polyadenylation sequences, et SV40, bovine growth hormone, and a selectable marker such as G418 or hygromycin for selection of stable transfectants.

Cytosolic preparations from transfected or transformed cells expressing such fusions may be employed. All of the above techniques that are useful for ligand identification are also useful in drug screening and drug development protocols.

Alternatively, the purified recombinant protein could be used to substitute for crude cell lysates in a competitive binding assay with MAPKAP kinase substrates. This assay is useful to screen for novel compounds which bind MAPKAP kinase, or as a way to assess alterations to compound which is known to bind. The availability of purified protein allows alternative configurations of the assay from those described previously for the crude material. For example, if the protein is covalently linked to a tag, such a protein binding site for configuration in a colorimetic assay, e.g., conjugated antibody, or to an enzyme for direct detection of enzyme activity, e.g., horseradish peroxidase or alkaline phosphatase, binding to novel compounds displayed on a solid matrix could be detected. Such compounds could include low molecular weight organic molecules, peptides, peptoids, and proteins. In the latter case, the protein can be used as a way to isolate other proteins in its signaling cascade, for example, those that are in the pathway for activation of cytokine translation in activated monocytes. The protein may also be used to isolate naturally occurring regulatory molecules within mammalian cells that act by a MAPKAP kinase binding mechanism. Finally, the protein can be used to identify target peptides displayed on the surface of phage.

The fact that MAPKAP kinases are protein kinases suggests that the recombinant forms can be used to establish a protein kinase activity assays. Typically, this would involve the direct incubation of MAPKAP kinase with a protein or peptide substrate in the presence of $\gamma$-$^{32}$P-ATP, followed by the measurement of radioactivity incorporated into the substrate by separation and counting. Separation methods include immunoprecipitation, conjugation of substrate to a bead allowing separation by centrifugation or determination of incorporation by scintillation proximity assay, SDS-PAGE followed by autoradiography or biosensor analysis. While all the native substrates are not yet known, useful substrates for screening purposes include MAPKAP kinase itself (autophosphorylation) HSP-25, HSP-27 and related peptides as well as peptides related to other known MAP kinase substrates. Other substances might be discovered by incubating MAPKAP kinases with random peptides conjugated to solid supports or displayed by phage (see above) or by incubation of MAPKAP kinases with mammalian cell lysates (e.g. THP.1 cell lysates) and $\gamma$-$^{32}$P-ATP, followed by separation of the labelled target proteins, and sequencing. The protein kinase activity of MAPKAP may require incubation with a specific CSBP. This may be achieved by preincubating with lysates from stimulated eukaryotic cells (e.g., LPS treated THP.1 cells) and ATP. More specifically, activated CSBP can be obtained by immunoprecipitation, fractionation following expression in yeast (Brewster, et al., (1993). Science 259, 1760–1762) or expression in mammalian cells stimulated with various cytokine or endotoxin treatments or by co-expression with an active MAPKAP kinase mutant (e.g., MKK3) or by activation in vitro using MAPKAP isolated from stimulated cells as described above for CSBP. The method also includes the use of MAPKAP kinase mutants which possess enhanced activity in the absence of activation.

These assays permit the discovery and modification of compounds which inhibit MAPKAP kinase activity in vitro. Such compounds would be expected to block cytokine synthesis in a comparable fashion to the CSAID™ compounds described herein. They could also lead to the discovery of novel substrates which themselves may be viable targets for discovery of novel compounds which block cytokine production.

These assays can be used to discover compounds which block the activation of CSBP or MAPKAP protein kinase activity and to improve the potency of already discovered compounds. These compounds would be expected to have utility due to their blocking of cytokine synthesis. The assays are also useful to discover novel MAP kinases which themselves may become targets for novel compounds which would block cytokine synthesis.

The ability of human CSBP to rescue a hog$^-$ deletion strain upon growth in conditions of high osmolarity allows for the direct screening of compounds which block CSBP activity in vivo. For example, compounds could be screened for their ability to block growth of a CSBP+lhog$^-$yeast strain in high osmolarity but which have no effect on growth of the same strain in standard osmolarity or on a CSBP-lHOG1$^+$ in high osmolarity. The sensitivity of the yeast based assay can be increased by introducing host mutations that affect the cell membrane and permeability (Gaber, et al., *Mol. Cell. Biol.* 9: 3447–3456. (1989). Once a yeast homolog for the MAPKAP kinase is identified, this method may be applied to screening of MAPKAP kinase inhibitors as well.

In a compound screening embodiment of this invention, the MAPKAP kinase is isolated, immobilized or cell bound form is contacted with a plurality of candidate molecules and those candidates are selected which bind to and interact with the protein. The binding or interaction can be measured directly by using radioactively labeled candidate of interest or indirectly by measuring an effect resulting from the interaction or binding of the candidate compound. Alternatively, the candidate compounds can be subjected to a competition screening assays, in which a known ligand, preferably labeled with an analytically detectable reagent, most notably radioactivity, is introduced with the compounds to be tested and the compound's capacity to inhibit or enhance the binding of the labeled ligand is measured. Compounds are screened for their increased affinity and selectivity for the MAPKAP kinase.

Further refinement of the binding assay to facilitate high throughout screening can be achieved by the minor modification of separating bound ligand from free ligand using spin columns.

This invention also contemplates pharmaceutical compositions comprising compounds when identified by the above methods and a pharmaceutically acceptable carrier. Pharmaceutical compositions of proteinaceous drugs of this invention are particularly useful for parenteral administration, i.e., subcutaneously, intramuscularly or intravenously. The compositions for parenteral administration will commonly comprise a solution of the compounds of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc. The concentration of the compound of the invention in such pharmaceutical formulation can very widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, *Remington's Pharmaceutical Science,* 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the identified drug is non-proteinaceous, it may be administered alone or in combination with pharmaceutically acceptable carriers. The proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form of troches or lozenges in which the active ingredient is mixed with sugar and corn syrups, flavoring agents and dyes; and then dehydrated sufficiently to make it suitable for pressing into a solid form. They may be administered orally in the form of solutions which may be injected parenterally, that is, intramuscularly, intravenously or subcutaneously. For parenteral administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. The physician will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other serotonergic agents and the dosage level is of the same order of magnitude as is generally employed with these other therapeutic agents. The therapeutic dosage will generally be from 1 to 10 milligrams per day and higher although it may be administered in several different dosage units. Tablets containing from 0.5 to 10 mg. of active agent are particularly useful. Generally, for all methods of use disclosed herein the daily oral and parenteral dosage regimen will preferably be from about 0.1 to about 80 mg/kg of total body weight.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

The nucleic acid embodiment of this invention is particularly useful in providing probes capable of specific hybridization with human MAPKAP kinase sequences. Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. This invention contemplates, for example using receptor encoding probes in the diagnostic evaluation of disease states characterized by an abnormal, i.e. increased or decreased level of receptor gene expression. Alternatively, the probes can be used to identify individuals carrying chromosomal or molecular mutations in the gene encoding the receptor. Depending on the conditions employed by the ordinary skilled artisan, the probes can be used to identify and recover additional examples of this receptor (in its genomic or cDNA form) from other cell types and individuals. As a general rule the more stringent the hybridization conditions the more closely related genes will be that are recovered.

Also within the scope of this invention are antisense oligonucleotides predicated upon the sequences disclosed herein for the MAPKAP kinase. Synthetic oligonucleotides or related antisense chemical structural analogs are designed to recognize and specifically bind to a target nucleic acid encoding the receptor gene and inhibit gene expression, e.g., the translation of the gene when the target nucleic acid is mRNA. Although not wishing to be bound to a particular theory for the mechanism of action of antisense drugs, it is believed that such drugs can act by one or more of the following mechanisms: by binding to mRNA and inducing degradation by endogenous nucleases such as RNase I or by inhibiting the translation of mRNA by inhibiting its binding to regulatory factors or ribosomal components necessary for productive protein synthesis. Additionally the antisense sequences can be use as components of a complex macromolecular arrays in which the sequences are combined with ribozyme sequences or reactive chemical groups and are used to specifically target mRNAs of interest and degrade or chemically modify said mRNAs. The general field of antisense technology is illustrated by the following disclosures which are incorporated herein by reference for purposes of background (Cohen, J. S., *Trends in Pharm. Sci.* 10:435 (1989) and Weintraub, H. M. *Scientific American Jan.*(1990) at page 40).

This invention also contemplates the use of the DNA sequences disclosed herein in gene therapy. Because MAPKAP kinase is a protein kinase, it is possible to make a site specific mutant which is inactive as a kinase but will block activation of the endogenous CSBP when coexpressed in the same cell, i.e., it is a dominant negative mutant (Kolch et al., *Nature* 349: 426–428 (1991). The DNA encoding this mutant protein could be used in gene therapy to reduce chronic inflammation. There are many vector and delivery systems available to direct DNA into target cells in vivo, e.g. adenovirus, retroviruses.

This invention also contemplates antibodies, monoclonal or polyclonal directed to epitopes corresponding to amino acid sequences disclosed herein from the MAPKAP kinase. Particularly important regions of the receptor for immunological purposes are those regions associated with ligand binding domains of the protein. Antibodies directed to the regions are particularly useful in diagnostic and therapeutic applications because of their effect upon protein-ligand interaction. Methods for the production of polyclonal and monoclonal antibodies are well known, see for example Chap. 11 of Ausubel et al. (supra).

This invention also provides pharmaceutical compositions comprising an effective amount of antibody or fragment thereof directed against the MAPKAP kinases to block binding of the naturally occurring ligands to that protein in order to treat or ameliorate disease states associated with protein activation.

Transgenic, non-human, animals may be obtained by transfecting appropriate fertilized eggs or embryos of a host with nucleic acids encoding the MAPKAP kinase disclosed herein, see for example U.S. Pat. Nos. 4,736,866; 5,175,385; 5,175,384 and 5,175,386. The resultant transgenic animal may be used as a model for the study of CSBP/MAPKAP kinase/ligand interaction. Particularly, useful transgenic animals are those which display a detectable phenotype associated with the expression of the protein. Drugs may then be screened for their ability to reverse or exacerbate the relevant phenotype. This invention also contemplates operatively linking the MAPKAP kinase coding gene to regulatory elements which are differentially responsive to various temperature or metabolic conditions, thereby effectively turning on or off the phenotypic expression in response to those conditions.

The nucleic acid probes disclosed herein can be used to clone the cognate version of the human MAPKAP kinase gene from a desired experimental animal species; for example the murine version. Strains of mice can be developed in which said gene has been eliminated by conventional gene knock-out technology. The gene can then be substituted/or replaced by the human MAPKAP kinase DNA of this invention to yield a mouse for screening candidate drugs in vivo. Similar gene knockout and human protein inhibition studies can also be performed with yeast.

The purified protein of this invention is also useful in a reagent for structural studies with and without bound drug candidates as a means for the rational design of novel drugs affecting MAPKAP kinase. For example, the recombinant protein may be used to derive the structure of the protein alone or complexed with CSBP and/or complexed with ligands and related compounds through X-ray crystallography, NMR or modeling from published structures of related protein kinases, e.g., CSK. A structure fosters an understanding of how the inhibitory compounds bind, and can lead to the design or discovery of further compounds which can block CSBP or MAPKAP kinase activity and hence be inhibitors of cytokine synthesis. There are now several examples of such structure-based design for other protein targets, e.g., HIV protease. Given the similarity of CSBP to several other kinases (e.g. the MAP and CDC kinases) such structural information will be useful in designing novel compounds which inhibit other members of the kinase family.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method for identifying at lest one compound as a mitogen activated protein kinase-activated protein (MAPKAP) kinase-3 inhibitor, said method comprising the steps of:

a. incubating purified, or enriched, active MAPKAP kinase-3 (SEQ ID NO:2) or a mixture of unactivated MAPKAP kinase-3 (SEQ ID NO:2) and active cytokine suppressive anti-inflammatory drug binding protein (CSBP) with peptide or protein substrate in the presence of labelled ATP, and said at least one compound;

b. measuring the incorporation of the labelled phosphorus into the peptide or protein substrate; and c. identifying a compound that reduces the amount of labelled phosphorus included in said substrate.

2. The method according to claim 1, wherein said CSBP is purified.

3. The method according to claim 1, wherein said CSBP is unactivated.

4. The method according to claim 1, wherein said CSBP and/or MAPKAP kinase-3 (SEQ ID NO:2) is chemically conjugated.

5. The method according to claim 1, wherein said CSBP is fluorescently labelled or radiolabelled.

6. A method for identifying at least one compound as a MAPKAP kinase-3 inhibitor, said method comprising the steps of:
   a. binding MAPKAP kinase-3 (SEQ ID NO:2) to a solid support;
   b. adding CSBP in the presence of said at least one compound;
   c. measuring the amount of said MAPKAP kinase-3 (SEQ ID NO:2) bound to said CSBP on said support;
   d. identifying a compound that reduces the amount of said MAPKAP kinase-3 (SEO ID NO:2) binding to said CSBP on said support.

7. The method according to claim 6, wherein the amount of said CSBP is detected by antibodies.

8. The method according to claim 6, wherein said CSBP binding is detected by surface plasmon resonance.

9. The method according to claim 6, wherein said MAPKAP kinase-3 (SEQ ID NO:2) and/or said CSBP is purified.

10. The method according to claim 6, wherein said CSBP and/or MAPKAP kinase-3 (SEQ ID NO:2) is fused or conjugated to a peptide or protein.

11. A method for identifying at least one compound that effects the interaction between CSBP and MAPKAP kinase-3 (SEQ ID NO:2), said method comprising the steps of:
   (a) forming permeabilized yeast-based two-hybrid screen for said interaction;
   (b) contacting said permeabilized yeast with said at least one compound; and
   (c) identifying a compound that blocks or inhibits yeast growth.

12. A method for identifying at least one compound as a MAPKAP kinase-3 inhibitor, said method comprising the steps of:
   a. binding CSBP to a solid support;
   b. adding MAPKAP kinase-3 (SEQ ID NO:2) in the presence of said at least one compound;
   c. measuring the amount of said CSBP bound to said MAPKAP kinase-3 (SEQ ID NO:2) on said support;
   d. identifying a compound that reduces the amount of said CSBP binding to said MAPKAP kinase-3 (SEQ ID NO:2) on said support.

13. The method according to claim 12, wherein the amount of said MAPKAP kinase-3 (SEQ ID NO:2) is detected by antibodies.

14. The method according to claim 12, wherein said MAPKAP kinase-3 (SEQ ID NO:2) binding is detected by surface plasmon resonance.

15. The method according to claim 12, wherein said MAPKAP kinase-3 (SEQ ID NO:2) and/or said CSBP is purified.

16. The method according to claim 12, wherein said CSBP and/or MAPKAP kinase-3 (SEQ ID NO:2) is fused or conjugated to a peptide or protein.

* * * * *